United States Patent
Koczo et al.

(10) Patent No.: US 8,809,404 B2
(45) Date of Patent: Aug. 19, 2014

(54) SILOXANE POLYETHER COPOLYMERS

(71) Applicant: Momentive Performance Materials Inc., Waterford, NY (US)

(72) Inventors: Kalman Koczo, Suffern, NY (US); Benjamin Falk, Yorktown Heights, NY (US); Mark Leatherman, Stamford, CT (US); Antonio Palumbo, Syracuse (IT)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 13/754,550

(22) Filed: Jan. 30, 2013

(65) Prior Publication Data

US 2013/0197108 A1    Aug. 1, 2013

Related U.S. Application Data

(60) Provisional application No. 61/593,450, filed on Feb. 1, 2012.

(51) Int. Cl.
*C10G 33/04* (2006.01)

(52) U.S. Cl.
USPC .......................................... 516/144; 556/446

(58) Field of Classification Search
None
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,299,112 A * | 1/1967 | Bailey | 556/445 |
| 3,573,334 A * | 3/1971 | Wheeler, Jr. | 556/444 |
| 3,677,962 A | 7/1972 | Koerner et al. | |
| 3,715,334 A | 2/1973 | Karstedt | |
| 3,775,452 A | 11/1973 | Karstedt | |
| 3,814,730 A | 6/1974 | Karstedt | |
| 3,867,420 A * | 2/1975 | Morehouse et al. | 556/420 |
| 4,059,606 A * | 11/1977 | Walsingham et al. | 556/444 |
| 4,183,820 A | 1/1980 | Theile et al. | |
| 4,596,653 A | 6/1986 | Graham et al. | |
| 4,962,218 A * | 10/1990 | Blevins et al. | 556/445 |
| 5,004,559 A | 4/1991 | Koerner et al. | |
| 5,110,970 A * | 5/1992 | Blevins et al. | 556/445 |
| 6,541,593 B1 * | 4/2003 | Jyono et al. | 528/15 |
| 7,259,220 B1 * | 8/2007 | Farris et al. | 528/15 |
| 7,745,501 B2 | 6/2010 | Koczo et al. | |
| 7,829,734 B2 * | 11/2010 | Farris et al. | 556/434 |
| 2002/0188058 A1 | 12/2002 | Chaiyawat et al. | |
| 2008/0009600 A1 | 1/2008 | Lu et al. | |
| 2008/0177000 A1 | 7/2008 | Ahn et al. | |
| 2011/0015075 A1 * | 1/2011 | Leatherman et al. | 504/358 |
| 2013/0123530 A1 * | 5/2013 | Boehm et al. | 556/423 |

FOREIGN PATENT DOCUMENTS

WO    2008121310    10/2008

OTHER PUBLICATIONS

J.L. Spier, "Homogeneous Catalysis of Hydrosilation by Transition Metals", in Advances in Organometallic Chemistry, 17: p. 407-447, F.G.A. Stone and R. West editors, published by Academic Press (New York 1979).
International Search Report from PCT/US2013/023898 dated Apr. 5, 2013.

* cited by examiner

*Primary Examiner* — Robert S Loewe
(74) *Attorney, Agent, or Firm* — Dominick G. Vicari; Joseph S. Ostroff

(57) ABSTRACT

The present invention is related to the preparation and use of moderately cross-linked (chin-extended), reverse (or "inverted") surfactants, wherein the reverse surfactants comprise a polyether backbone with oligomeric or polymeric silicon-containing substitutions along the backbone. The present invention further describes crosslinked versions of the inverted surfactants, reaction products of alkenyl (allyl, vinyl, methallyl) functional copolymers (polyethers), silicone hydrides and cross-linking agents, which may be optionally reacted with water to react the remaining alkoxy groups. The crosslinking agent contains either SiH or Si-alkoxy groups or both. The compounds of the present invention exhibit only moderate cross-linking in order to be soluble or dispersible in appropriate solvents.

22 Claims, No Drawings

SILOXANE POLYETHER COPOLYMERS

RELATED APPLICATION DATA

This application claims benefit to U.S. Provisional Application No. 61/593,450, filed Feb. 1, 2012, of which the entire contents of the application are incorporated by reference herein.

FIELD OF THE INVENTION

The present invention relates to compositions containing copolymers, processes for their preparation and methods of use. Further, the present invention is related to the preparation and use of moderately cross-linked (chain-extended), reverse (or "inverted") surfactants in contrast to traditional silicone surfactants that contain a siloxane backbone and polyether substitutions on it (pendant, or at the end of the chain(s)). The reverse surfactants of the present invention comprise a polyether backbone with oligomeric or polymeric silicon containing substitutions. The present invention describes cross-linked versions of the inverted surfactants, described as reaction products of alkenyl (allyl, vinyl, methallyl) functional copolymers (polyethers), silicone hydrides and a cross-linking agent, that is optionally reacted with water to react the remaining alkoxy groups. The cross-linking agent contains either SiH or Si-alkoxy groups or both. The compounds of the present invention exhibit only moderate cross-linking in order to be soluble in appropriate solvents.

BACKGROUND OF THE INVENTION

It is well known that emulsions often cause difficulties in industrial processing operations. For this reason, the emulsified components need to be separated. Often, one or more chemicals, known as demulsifiers, are used for this purpose. For example, during crude oil processing, it is commonplace for water to become emulsified in the oil. The emulsified water is problematic from several standpoints, most notably as a corrosive to pipelines and as a disruptor to oil distillation processes. The resulting water-in-oil emulsion is typically highly stable as a result of natural surfactants (e.g., naphthenic acids, asphaltenes, and resins) and solid particles in the crude oil.

To disrupt the stabilized water-in-oil emulsions in crude oil, not only organic, but also silicon based demulsifiers can be used. See, for example, U.S. Pat. Nos. 5,004,559, 4,596,653, 4,183,820, and 3,677,962, all of which disclose the use of polyoxyalkylene-polysiloxane copolymers as demulsifiers in crude oil or petroleum processing. However, there remains a need for demulsifiers capable of breaking and/or separating such emulsions more effectively.

SUMMARY OF THE INVENTION

The present invention provides for a soluble or dispersible copolymer composition, comprising the reaction products of
(a) a copolymer having the following formula

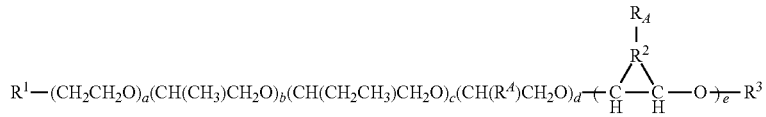

where $R^4$ is a monovalent group containing at least one terminal alkenyl group, such as allyl ($-CH_2-CH=CH_2$), vinyl ($-CH=CH_2$) or methallyl ($-C(CH_3)=CH_2$) group, optionally containing heteroatoms and hydroxyl groups, $R^1$ is selected from $-OH$, $-OC(O)CH_3$ or a monovalent hydrocarbon radical, optionally containing heteroatoms and hydroxyl groups, having from about 1 to about 40 carbon atoms, $R^2$ is a trivalent hydrocarbon radical optionally containing heteroatoms and hydroxyl groups, having from about 3 to about 40 carbon atoms, $R^3$ is selected from hydrogen, a $-C(O)CH_3$ group or a monovalent hydrocarbon radical optionally containing heteroatoms and hydroxyl groups, having from about 1 to about 40 carbon atoms, subscripts a, b, c, d and e are subject to the limitation $3<a+b+c+d+e<$ about 1000 and subscripts $d+e \geq 2$, (b) a silicone hydride having the following formula $M_f M^H_g D_h D^H_i T_j T^H_k Q_l$ with $M=R^4R^5R^6SiO_{1/2}$,
$M^H=R^7R^8HSiO_{1/2}$,
$D=R^9R^{10}SiO_{2/2}$,
$D^H=R^{11}HSiO_{2/2}$,
$T=R^{12}SiO_{3/2}$,
$T^H=HSiO_{3/2}$,
$Q=SiO_{4/2}$, $R^4$, $R^5$, $R^6$, $R^7$, $R^8$, $R^9$, $R^{10}$, $R^{11}$ and $R^{12}$ are each independently selected from the groups of $OR^{13}$ or monovalent hydrocarbon radicals, optionally containing heteroatoms and hydroxyl groups, having from about 1 to about 20 carbon atoms, $R^{13}$ is selected from the group of H or monovalent hydrocarbon radicals optionally containing heteroatoms and hydroxyl groups, having from about 1 to about 20 carbon atoms, subscripts f, g, h, i, j, k and l are subject to the limitation $2<f+g+h+i+j+k+l<$ about 300, and $g+i+k \geq 1$, and (c) a cross-linking agent.

The present invention further provides for processes to demulsify emulsions utilizing the compositions of the present invention.

DETAILED DESCRIPTION OF THE INVENTION

In the specification and claims herein, the following terms and expressions are to be understood as indicated.

The expression "hydrocarbon radicals" means any hydrocarbon group from which one or more hydrogen atoms have been removed and is inclusive of alkyl, alkenyl, alkynyl, cyclic alkyl, cyclic alkenyl, cyclic alkynyl, aryl, aralkyl and arenyl, and optionally it is substituted with oxygen, nitrogen, or sulfur.

The term "alkyl" means any monovalent, saturated, straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all sub-ranges within that range and any combination of the various endpoints or intermediate elements of such ranges or sub-ranges. It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

Other optional ingredients may be added in the compositions of the present invention including coupling agents, e.g., silane coupling agents, curing aids, e.g., including activators, retarders and accelerators, processing additives such as oils, plasticizers, tackifying resins, silicas, other fillers, pigments, fatty acids, metal oxides, waxes, antioxidants and antiozonants, peptizing agents, reinforcing materials such as, for example, carbon black; wetting agents, anticorrosion additives, hydrogen sulfide scavengers, biocides and so forth. Such additives are selected based upon the intended use and such selection is within the knowledge of one of skill in the art, as are the required amounts of such additives known to one of skill in the art.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example finely divided solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

As used herein, integer values of stoichiometric subscripts refer to molecular species and non-integer values of stoichiometric subscripts refer to a mixture of molecular species on a molecular weight average basis, a number average basis or a mole fraction basis.

For the purpose of this disclosure, the term "soluble" means that a liquid or solid material forms a clear solution or dispersion with another liquid.

According to the invention, there is provided a cross-linked copolymer composition, which is soluble or dispersible in appropriate solvents, and comprises the reaction products of (a) a copolymer having the following formula

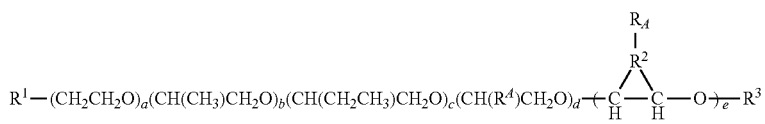

where $R^A$ is a monovalent group containing at least one terminal alkenyl group, such as allyl ($-CH_2-CH=CH_2$), vinyl ($-CH=CH_2$) or methallyl ($-C(CH_3)=CH_2$) group, optionally containing heteroatoms and hydroxyl groups, $R^1$ is selected from $-OH$, $-OC(O)CH_3$ or a monovalent hydrocarbon radical, optionally containing heteroatoms and hydroxyl groups, having from about 1 to about 40 carbon atoms, preferably from about 1 to about 30 carbon atoms, and more preferably from about 1 to about 20 carbon atoms, $R^2$ is a trivalent hydrocarbon radical optionally containing heteroatoms and hydroxyl groups, having from about 3 to about 40 carbon atoms, preferably from about 3 to about 30 carbon atoms, and more preferably from about 3 to about 20 carbon atoms, $R^3$ is selected from hydrogen, a —C(O)CH$_3$ group or a monovalent hydrocarbon radical optionally containing heteroatoms and hydroxyl groups, having from about 1 to about 40 carbon atoms, preferably from about 1 to about 30 carbon atoms, and more preferably from about 1 to about 20 carbon atoms, subscripts a, b, c, d and e are subject to the limitation 3<a+b+c+d+e<about 1000 and subscripts d+e≥2, (b) a silicone hydride having the following formula $$M_f M^H_g D_h D^H_i T_j T^H_k Q_l \text{ with}$$

$M = R^4 R^5 R^6 SiO_{1/2}$,
$M^H = R^7 R^8 HSiO_{1/2}$,
$D = R^9 R^{10} SiO_{2/2}$,
$D^H = R^{11} HSiO_{2/2}$,
$T = R^{12} SiO_{3/2}$,
$T^H = HSiO_{3/2}$,
$Q = SiO_{4/2}$, $R^4$, $R^5$, $R^6$, $R^7$, $R^8$, $R^9$, $R^{10}$, $R^{11}$ and $R^{12}$ are each independently selected from the groups of $OR^{13}$ or monovalent hydrocarbon radicals, optionally containing heteroatoms and hydroxyl groups, having from about 1 to about 20 carbon atoms, preferably from about 1 to about 15 carbon atoms, and more preferably from about 1 to about 10 carbon atoms, $R^{13}$ is selected from the group of H or monovalent hydrocarbon radicals optionally containing heteroatoms and hydroxyl groups, having from about 1 to about 20 carbon atoms, preferably from about 1 to about 15 carbon atoms, and more preferably from about 1 to about 10 carbon atoms, subscripts f, g, h, i, j, k and l are subject to the limitation 2<f+g+h+i+j+k+l<about 300, and g+i+k≥1, and (c) a cross-linking agent.

Another aspect of the present invention is that the cross-linking agent component (c) is a silicone hydride, having the following formula $$M_m M^H_n D_o D^H_p T_q T^H_r Q_s \text{ where}$$

$M = R^{14} R^{15} R^{16} SiO_{1/2}$,
$M^H = R^{17} R^{18} HSiO_{1/2}$,
$D = R^{19} R^{20} SiO_{2/2}$,
$D^H = R^{21} HSiO_{2/2}$,
$T = R^{22} SiO_{3/2}$,
$T^H = HSiO_{3/2}$,
$Q = SiO_{4/2}$, $R^{14}$, $R^{15}$, $R^{16}$, $R^{17}$, $R^{18}$, $R^{19}$, $R^{20}$, $R^{21}$ and $R^{22}$ are each independently selected from the groups of $OR^{23}$ or monovalent hydrocarbon radicals, optionally containing heteroatoms and hydroxyl groups, having from about 1 to about 20 carbon atoms, preferably from about 1 to about 15 carbon atoms, and more preferably from about 1 to about 10 carbon atoms, subject to the limitation that the sum of the SiH and $OR^{23}$ groups in cross-linking agent (c) is more than one, $R^{23}$ is independently selected from the group of H or monovalent hydrocarbon radicals, optionally containing heteroatoms and hydroxyl groups, having from about 1 to about 20 carbon atoms, preferably from about 1 to about 15 carbon atoms, and more preferably from about 1 to about 10, carbon atoms, subscripts m, n, o, p, q, r and s are subject to the limitation 1≤m+n+o+p+q+r+s<about 300.

Another aspect of the present invention is that cross-linking agent (c) is an organosilane, having the following formula:

$$R^{24} R^{25} R^{26} SiH, \text{ with}$$

$R^{24}$, $R^{25}$ and $R^{26}$ each independently selected from the groups of H or monovalent hydrocarbons having from about 1 to about 15 carbon atoms, preferably from about 1 to about 12 carbon atoms and more preferably from about 1 to about 10 carbon atoms, optionally containing nitrogen or oxygen or $OR^{27}$, subject to the limitation that the sum of the SiH and $OR^{27}$ groups in cross-linking agent (c) is more than one, $R^{27}$ is independently selected from H or monovalent hydrocarbons having from about 1 to about 15 carbon atoms, preferably from about 1 to about 12 carbon atoms and more preferably from about 1 to about 10 carbon atoms, optionally containing nitrogen or oxygen.

Another aspect of the present invention is the reaction product of the present invention obtained by using silicon hydride (b) having the following formula:

$$MD_t D^H_u M$$

wherein
$M = R^{28} R^{29} R^{30} SiO_{1/2}$,
$D = R^{31} R^{32} SiO_{2/2}$,
$D^H = R^{33} HSiO_{2/2}$, $R^{28}$, $R^{29}$, $R^{30}$, $R^{31}$, $R^{32}$ and $R^{33}$ are each independently selected from the groups of $OR^{34}$ or monovalent hydrocarbon radicals, optionally containing heteroatoms and hydroxyl groups, having from about 1 to about 20 carbon atoms, $R^{34}$ is independently selected from the group of H or monovalent hydrocarbon radicals, optionally containing heteroatoms and hydroxyl groups, having from about 1 to about 20 carbon atoms, subscripts t and u are subject to the limitation 1≤t+u<about 300 and 1≤u.

Another aspect of the present invention is the reaction product of the present invention obtained by using cross-linking agent (c) having the following formula:

$$MD_v D^H_w M$$

wherein
$M = R^{35} R^{36} R^{37} SiO_{1/2}$,
$D = R^{38} R^{39} SiO_{2/2}$,
$D^H = R^{48} HSiO_{2/2}$, $R^{35}$, $R^{36}$, $R^{37}$, $R^{38}$, $R^{39}$ and $R^{40}$ are each independently selected from the groups of $OR^{41}$ or monovalent hydrocarbon radicals, optionally containing heteroatoms and hydroxyl groups, having from about 1 to about 20 carbon atoms, subject to the limitation that the sum of the SiH and $OR^{41}$ groups in cross-linking agent (c) is more than one;

$R^{41}$ is independently selected from the group of H or monovalent hydrocarbon radicals optionally containing heteroatoms and hydroxyl groups, having from about 1 to about 20 carbon atoms, subscripts v and w are subject to the limitation 1≤v+w<about 300.

The copolymers of the present invention can be formed by the reaction of the terminal alkenyl groups (i.e. vinyl, allyl or methallyl etc.) of copolymer (a) with the SiH groups of silicone hydride (b) and cross-linking agent (c) through the hydrosilylation reaction by using catalysts known in the art. Precious metal catalysts suitable for hydrosilylation or olefin addition reactions are well known in the art and comprise complexes of rhodium, ruthenium, palladium, osmium, iridium, and platinum or mixtures thereof. Many types of platinum catalysts for this SiH olefin addition reaction are known and such platinum catalysts may be used to generate the compositions of the present invention. The platinum compound can be selected from those having the formula ($PtCl_2Olefin$) and $H(PtCl_3Olefin)$ as described in U.S. Pat. No. 3,159,601, hereby incorporated by reference. A further platinum containing material can be a complex of chloroplatinic acid with up to 2 moles per gram of platinum of a member selected from the class consisting of alcohols, ethers, aldehydes and mixtures thereof as described in U.S. Pat. No. 3,220,972 hereby incorporated by reference. Yet another group of platinum containing materials useful in this present invention is described in U.S. Pat. Nos. 3,715,334; 3,775,452 and 3,814,730 (Karstedt). Additional background concerning the art may be found in J. L. Spier, "Homogeneous Catalysis of Hydrosilation by Transition Metals", in Advances in Organometallic Chemistry, volume 17, pages 407 through 447, F. G. A. Stone and R. West editors, published by Academic Press (New York, 1979). Those skilled in the art can easily determine an effective amount of platinum catalyst and the optimum reaction conditions. Generally an effective amount of catalyst ranges from about 0.1 to 50 parts per million of the total copolymer composition.

In another embodiment of the invention the reaction products of the hydrosilation reaction above can be further reacted with water, if the silicone hydride (b) or the cross-linking agent (c) contained alkoxy-silane group(s).

The three components forming the copolymers of the present invention can be reacted using various orders of addition:

Copolymer (a) can be added first and then reacted it with silicone hydride (b), and then the reaction products can be further reacted with a cross-linking agent (c), or Copolymer (a) can be added first and then reacted with a cross-linking agent (c) and then the reaction products can be further reacted with silicone hydride (b), or The three components, (a), (b) and (c) can be all charged and reacted in one step.

Further combinations, for example, partially dosing the components etc., can be also used, which are obvious for one skilled in the art.

After these reactions in the previous sections, cross-linked copolymers form. Another aspect of the invention is that the cross-linking reactions do not lead to a three-dimensional polymer network inside the entire material and therefore the copolymers in the present invention are soluble in appropriate solvents. Examples of such solvents are isopropanol, toluene, xylenes, propylene glycol and similar solvents.

Another aspect of the invention is that the cross-linked copolymers in the present invention are pourable liquids, either at ambient temperature or they are solids, which can be melted to become pourable liquids.

Applications for Embodiments of the Invention

Emulsions can create problems in many industrial applications because the emulsions often do not separate into the liquid components for a prolonged time. In this case typically chemical additives, so-called demulsifying agents, are added to initiate, accelerate and complete the separation process. Demulsifying agents break emulsions and mixtures of polar solutes like water, and non-polar solvents like oil.

Demulsifiers are used to separate emulsions into polar (typically water) and non-polar liquids by incorporating the demulsifying agent into the emulsion. Demulsifiers are known in the art and usually comprise blends of surface-active chemicals. Typical organic demulsifier structures include, but are not limited to sulfonates, sulfosuccinates, polyol esters, polyester amines, polymeric elastomers, sulfated polyol ester, oxyalkylated phenolic resins, alkylphenol alkoxylates, amine alkoxylates, quaternary amines, ethoxylated amines, bisamides, polyalkylene glycols, polymerized polyols, resin esters, polyether polyols, resin alkoxylates, modified polyols, polyimine alkoxylates and diepoxides.

The compositions of the present invention may be utilized in mining and petroleum processing applications, especially for demulsification. Using the compositions of the present invention for demulsifying is accomplished by i. incorporating a demulsifying-effective amount of the copolymer composition of the present invention into an emulsion including crude oil or the like;

ii. allowing the emulsion to separate into at least two phases; and iii. separating said at least two phases from each other.

The compositions described in the present invention can be used for demulsifying alone or accompanied by additional silicone and/or organic demulsifiers and these components can be utilized in the form of a blend, a solution, a dispersion, or either an oil-in-water or a water-in-oil emulsion or microemulsion or the various demulsifying agents can be added separately. When applied in solution suitable solvents can be selected from linear or branched, cyclic or acyclic, saturated or unsaturated, aliphatic or aromatic hydrocarbons, alcohol, ketones, esters, ethers and their blends or whatever solvent is commonly used in the particular application.

When the organic and/or silicone demulsifier is included, the weight ratio of the compositions of the present invention to the organic and silicone demulsifier is typically in the range of about 100:1 to about 1:1000, more typically in the range of about 5:1 to about 1:200.

The method of separating emulsions comprises the incorporation of a demulsifying-effective amount of demulsifier into the emulsion, allowing the emulsion to separate into at least two phases and separating these at least two phases from each other. The incorporation of the demulsifier into the emulsion to be separated can be achieved by any method known in the art for integrally mixing the demulsifier with the emulsion. The mixing procedure can use, for example, standard mixers, high-speed mixers or blenders, or shakers. The temperature can be unadjusted within room temperature limits (~20-40° C.), or adjusted as required, for example, to 40-150° C. for a suitable amount of time.

A. Mining and Petroleum Industry

A typical application of the compositions in the present invention is the separation of crude oil emulsions. During extraction and production of crude oil, water or brine gets emulsified into the crude oil yielding a water-in-oil emulsion, which can be unstabilized or stabilized by surface active materials, organic solids, such as asphaltenes and resins, or inorganic solids. This water-in-oil emulsion gives rise to several downstream problems; corrosion during refinery processes, disruption of distillation processes and greater energy requirement to pump the more viscous emulsion are to name a few. Thus, demulsifiers are extensively used in the petroleum industry to break water-in-oil and oil-in-water emulsions; and before transportation, refining or processing the water content of the crude oil has to be reduced to pipeline specification levels (typically less than 0.05-2%) and this is typically achieved by injecting demulsifiers into the well, into the crude oil stream, at the separation equipment or at any other suitable points.

The compositions of the present invention will cause improved demulsifying action in the mining and petroleum industries, both in the oil field and refineries, including, but not limited to gas/oil and gas/oil/water separators, regular oil separators; desalters; bitumen extraction from oils sands (separating bitumen froth and solvent diluted bitumen emulsions); in steam assisted gravity drainage (SAGD); in enhanced oil recovery with surfactants and/or polymers or using supercritical carbon dioxide; in the separation of waste oils, slop oils, sludges, such as oily waste from desalters, waste water skimmings, refinery and petrochemical plant waste (tank bottom washes, coker drum waste, "dirty bleeds" etc.), steel and aluminum industrial waste, including synthetic lubes, high lithium grease, lube oil from rollers, metalworking fluid waste and paper plant waste.

Dehazing (demulsification) of lubrication oils and lubrication oil waste, such as automotive waste (motor oil etc.), bunker oil are also possible applications of the compositions in the present invention.

The compositions of the present invention can be also applied in emulsion preventors ("non-emulsifiers") in drilling, fracturing and well completion operations.

Another typical industrial use of the reaction products in the present invention is diesel fuel (including bio-diesel) dehazing when the demulsifier eliminates small amounts of emulsified water from the diesel fuel and diesel fuel antifoaming.

The compositions of the present invention will improve ore recovery from mining operations. The inclusion of the present compositions to mining processes such as flocculation, separation, purification, concentration, leaching and chemical extraction improves the separation of minerals from their gangue.

Further applications of the present invention in oil and gas include asphaltene dispersants and drag reduction.

The compositions of the present invention can be also used as foam control agents (defoamers, antifoams, deaerators) in gas/oil and gas/oil/water separators, crude oil processing, diesel fuel, and lubrication oil.

B. Water Processing

Compositions of the present invention are useful for applications involving commercial and industrial open recirculating cooling water towers, closed cooling water systems, cooling water conduits, heat exchangers, condensers, once-through cooling systems, pasteurizers, air washers, heat exchange systems, air conditioning/humidifiers/dehumidifiers, hydrostatic cookers, safety and/or fire water protection storage systems, water scrubbers, disposal wells, influent water systems, including filtration and clarifiers, wastewater treatment, wastewater treatment tanks, conduits, filtration beds, digesters, clarifiers, holding ponds, settling lagoons, canals, odor control, ion exchange resin beds, membrane filtration, reverse osmosis, micro- and ultra-filtration, assisting in the removal of biofilms in cooling tower applications, heat exchangers and process water systems, and the like.

SYNTHETIC EXAMPLES

Preparation Example 1

Poly(co-ethyleneoxide-allyl glycidyl ether) with the average structure $HO(CH_2CH_2O)_{60.0}(CH2CH(CH_2OCH_2CH=CH_2)O)_{5.0}H$ (100.0 g, 148 mmol allyl) was charged into a 4-necked 250 mL round bottom flask, which was equipped with an overhead stirrer, thermocouple, Friedrich's condenser with nitrogen inlet, and a glass stopper. The mixture was heated to 85° C., then trimethoxysilane (0.91 g, 7.4 mmol) and Karstedt's catalyst (diluted 1:9 in hexane, 5 ppm Pt) were added.

The glass stopper was then replaced with addition funnel filled with 1,1,1,3,5,5,5-heptamethyl trisiloxane (31.35 g, 141 mmol) and it was added over 10 minutes, and the mixture was heated overnight at 85° C. Then distilled water (5.0 g, 278 mmol) was added to quench any remaining trimethoxysilane and the reaction mixture was kept at 85° C. for 2.0 hrs. Dibutylamino ethanol (0.25 mL, 0.16 wt %) was added and the mixture was stirred for 1 hour then it was vacuum stripped at 120° C., 50 torr for 3.0 hrs using a nitrogen sparge tube and a 90 degree inlet adapter attached to the vacuum line. A yield of 117.4 g (88.7%) of brown-gray wax was obtained at room temperature. The product was soluble in isopropanol and toluene, and at 49° C. it was a pourable liquid with 2000 cP viscosity (measured with a Brookfield RV viscometer).

Preparation Example 2

Poly(co-ethyleneoxide-allyl glycidyl ether) with the average structure $HO(CH_2CH_2O)_{60.0}(CH2CH(CH_2OCH_2CH=CH_2)O)_{5.0}H$ (100.01 g, 130 mmol allyl), polymethylhydrogen siloxane $(CH_3)_3SiO[Si(CH_3)(H)O]_nSi(CH_3)_3$ (n is approximately 1.9) (7.25 g, 47 mmol), and toluene (30.41 g, 20.0 wt %) were charged into a 4-necked 250 mL round bottom flask, which was equipped with an overhead stirrer, thermocouple, Friedrich's condenser with nitrogen inlet, and a glass stopper. The mixture was heated to 85° C., then Karstedt's catalyst (diluted 1:9 in hexane, 10 ppm Pt) was added and the mixture was stirred for 1.0 hour. The reaction mixture was checked for hydrogen siloxanes by adding an aliquot to a fermentation tube filled with potassium hydroxide in ethanol. When no bubbles were detected it indicated that no hydrogen siloxanes were present.

Then further Karstedt's catalyst (diluted 1:9 in hexane, 10 ppm Pt) was added and the glass stopper was replaced with an addition funnel filled with 1,1,1,3,5,5,5-heptamethyl trisiloxane (14.87 g, 66.8 mmol). The first half of 1,1,1,3,5,5,5-heptamethyl trisiloxane was added in one minute and then the addition was stopped until the liquid cooled to 87° C. The rest of 1,1,1,3,5,5,5-heptamethyl trisiloxane was added in seven minutes, and the mixture was stirred and heated at 85° C. for 2.0 hours, and then cooled to room temperature overnight. Then the mixture was stripped at 50 torr vacuum at 120° C. for 2 hours in a rotary evaporator. The product was an amber oil at 50° C., which solidified into a wax at room temperature. The product was soluble in isopropanol and toluene, and at 50° C. it was a pourable liquid with 1710 cP viscosity (measured with a Brookfield RV viscometer).

Preparation Example 3

Poly(co-ethyleneoxide-allyl glycidyl ether) with the average structure $HO(CH_2CH_2O)_{60.0}(CH2CH(CH_2OCH_2CH=CH_2)O)_{5.0}H$ (100.01 g, 130 mmol allyl), polymethylhydrogen siloxane $(CH_3)_3SiO[Si(CH_3)(H)O]_nSi(CH_3)_3$ (n is approximately 1.9) (3.74 g, 24 mmol), and toluene (30.41 g, 20.0 wt %) were charged into a 4-necked 250 mL round bottom flask, which was equipped with an overhead stirrer, thermocouple, Friedrich's condenser with nitrogen inlet, and a glass stopper. The mixture was heated to 85° C., then Karstedt's catalyst (diluted 1:9 in hexane, 10 ppm Pt) was added and the mixture was stirred for 1.0 hour. The reaction mixture was checked for hydrogen siloxanes by adding an aliquot to a fermentation tube filled with potassium hydroxide in ethanol. When no bubbles were detected it indicated that no hydrogen siloxanes were present.

Then further Karstedt's catalyst (diluted 1:9 in hexane, 10 ppm Pt) was added and the glass stopper was replaced with an addition funnel filled with 1,1,1,3,5,5,5-heptamethyl trisiloxane (17.88 g, 79.4 mmol). The first half of 1,1,1,3,5,5,5-heptamethyl trisiloxane was added in one minute and then the addition was stopped until the liquid cooled to 87° C. The rest of 1,1,1,3,5,5,5-heptamethyl trisiloxane was added in seven minutes, and the mixture was stirred and heated at 85° C. for 2.0 hours, and then cooled to room temperature overnight. Then the mixture was stripped at 50 torr vacuum at 120° C. for 2 hours in a rotary evaporator. The product was an amber oil at 50° C., which solidified into a wax at room temperature. The product was soluble in isopropanol and toluene, and at 50° C. it was a pourable liquid with 469 cP viscosity (measured with a Brookfield RV viscometer).

Preparation Example 4

Poly(co-ethyleneoxide-allyl glycidyl ether) with the average structure $HO(CH_2CH_2O)_{60.0}(CH2CH(CH_2OCH_2CH=CH_2)O)_{5.0}H$ (81.7 g, 106 mmol allyl), polymethylhydrogen siloxane $(CH_3)_3SiO[Si(CH_3)(H)O]_nSi(CH_3)_3$ (n is approximately 1.9) (2.98 g, 19.5 mmol), and toluene (31.0 g, 20.0 wt %) were charged into a 4-necked 250 mL round bottom flask, which was equipped with an overhead stirrer, thermocouple, Friedrich's condenser with nitrogen inlet, and a glass stopper. The mixture was heated to 85° C., then Karstedt's catalyst (diluted 1:9 in hexane, 10 ppm Pt) was added and the mixture was stirred for 1.0 hour. The reaction mixture was checked for hydrogen siloxanes by adding an aliquot to a fermentation tube filled with potassium hydroxide in ethanol. When no bubbles were detected it indicated that no hydrogen siloxanes were present.

Then further Karstedt's catalyst (diluted 1:9 in hexane, 10 ppm Pt) was added and the glass stopper was replaced with an addition funnel filled with 1,1,1,3,5,5,5-heptamethyl trisiloxane (16.20 g, 72.8 mmol). The first half of 1,1,1,3,5,5,5-heptamethyl trisiloxane was added in one minute and then the addition was stopped until the liquid cooled to 87° C. The rest of 1,1,1,3,5,5,5-heptamethyl trisiloxane was added in seven minutes, and the mixture was stirred and heated at 85° C. for 2.0 hours, and then cooled to room temperature overnight. Then the mixture was stripped at 50 torr vacuum from 23° C. to 90° C. for 0.82 hours, then at 90° C., 50 torr for 1.0 hour using a nitrogen sparge tube and a 90 degree inlet adapter attached to the vacuum line. After re-pressurization the flask, a 1.00 g sample was analyzed on a Mettler Toledo Moisture Analyzer (130° C., setting=3) and 99.60% solids were found. The product was an amber oil at 50° C., which solidified into a wax at room temperature. The product was soluble in isopropanol and toluene, and at 50° C. it was a pourable liquid with 660 cP viscosity (measured with a Brookfield RV viscometer).

Preparation Example 5

Poly(co-ethyleneoxide-allyl glycidyl ether) with the average structure $HO(CH_2CH_2O)_{60.0}(CH2CH(CH_2OCH_2CH=CH_2)O)_{5.0}H$ (100.0 g, 157 mmol allyl), polymethylhydrogen siloxane $(CH_3)_3SiO[Si(CH_3)(H)O]_nSi(CH_3)_3$ (n is approximately 1.9) (3.25 g, 21.3 mmol), and toluene (25.3 g, 20.0 wt %) were charged into a 4-necked 250 mL round bottom flask, which was equipped with an overhead stirrer, thermocouple, Friedrich's condenser with nitrogen inlet, and a glass stopper. The mixture was heated to 85° C., then Karstedt's catalyst (diluted 1:9 in hexane, 8 ppm Pt) was added and the mixture was stirred for 0.83 hours. The reaction mixture was checked for hydrogen siloxanes by adding an aliquot to a fermentation tube filled with potassium hydroxide in ethanol. When no bubbles were detected it indicated that no hydrogen siloxanes were present.

Further Karstedt's catalyst (diluted 1:9 in hexane, 8 ppm Pt) was added and then 1,1,1,3,5,5,5-heptamethyl trisiloxane (21.3 g, 95.7 mmol) was added in portions over a ten-minute period and then stirred and heated at 85° C. for 2.0 hours, and cooled to room temperature overnight. The reaction mixture was then vacuum stripped at 50 torr from 24° C. to 90° C. for 0.42 hours, then at 90° C., 50 torr for 1.0 hour using a nitrogen sparge tube and a 90 degree inlet adapter attached to the vacuum line. After re-pressurization the flask, a 1.00 g sample was analyzed on a Mettler Toledo Moisture Analyzer (130° C., setting=3) and 99.70% solids were found. The product was a golden oil, which solidified into a gray wax at room temperature. The product was soluble in isopropanol and toluene, and at 50° C. it was a pourable liquid with 556 cP viscosity (measured with a Brookfield RV viscometer).

Preparation Example 6

Poly(co-ethyleneoxide-allyl glycidyl ether) with the average structure $HO(CH_2CH_2O)_{60.0}(CH2CH(CH_2OCH_2CH=CH_2)O)_{5.0}H$ (100.0 g, 157 mmol allyl), polymethylhydrogen siloxane $(CH_3)_3SiO[Si(CH_3)(H)O]_nSi(CH_3)_3$ (n is approximately 1.9) (3.60 g, 23.6 mmol), and toluene (32.4 g, 20.0 wt %) were charged into a 4-necked 250 mL round bottom flask, which was equipped with an overhead stirrer, thermocouple, Friedrich's condenser with nitrogen inlet, and a glass stopper. The mixture was heated to 85° C., then Karstedt's catalyst (diluted 1:9 in hexane, 8 ppm Pt) was added and the mixture was stirred for 0.75 hours. The reaction mixture was checked for hydrogen siloxanes by adding an aliquot to a fermentation tube filled with potassium hydroxide in ethanol. When no bubbles were detected it indicated that no hydrogen siloxanes were present.

Then further Karstedt's catalyst (diluted 1:9 in hexane, 8 ppm Pt) was added and the glass stopper was replaced with an addition funnel filled with 1,1,1,3,5,5,5-heptamethyl trisiloxane (25.70 g, 115.5 mmol). The 1,1,1,3,5,5,5-heptamethyl trisiloxane was added over a sixteen-minute period and then stirred and heated at 85° C. for 2.0 hours, and cooled to 72° C. The reaction mixture was then vacuum stripped at 50 torr from 72° C. to 90° C. for 0.5 hours, then at 90° C., 50 torr for 1.0 hour using a nitrogen sparge tube and a 90 degree inlet adapter attached to the vacuum line. After re-pressurization the flask, a 1.00 g sample was analyzed on a Mettler Toledo Moisture Analyzer (130° C., setting=3) and 99.70% solids were found. A yield of 121.8 g (94.2%) of an amber oil at 50° C. was obtained, which solidified into a gray wax at room temperature. The product was soluble in isopropanol and toluene, and at 50° C. it was a pourable liquid with 565 cP viscosity (measured with a Brookfield RV viscometer).

Preparation Example 7

Poly(co-ethyleneoxide-allyl glycidyl ether) with the average structure $HO(CH_2CH_2O)_{60.0}(CH2CH(CH_2OCH_2CH=CH_2)O)_{5.0}H$ (100.0 g, 157 mmol allyl), polymethylhydrogen siloxane $(CH_3)_3SiO[Si(CH_3)(H)O]_nSi(CH_3)_3$ (n is approximately 1.9) (2.40 g, 15.7 mmol), and toluene (32.4 g, 20.0 wt %) were charged into a 4-necked 250 mL round bottom flask, which was equipped with an overhead stirrer, thermocouple, Friedrich's condenser with nitrogen inlet, and a glass stopper. The mixture was heated to 85° C., then Karstedt's catalyst (diluted 1:9 in hexane, 8 ppm Pt) was added and the mixture was stirred for 0.92 hours. The reaction mixture was checked for hydrogen siloxanes by adding an aliquot to a fermentation tube filled with potassium hydroxide in ethanol. When no bubbles were detected it indicated that no hydrogen siloxanes were present.

Then further Karstedt's catalyst (diluted 1:9 in hexane, 8 ppm Pt) was added and the glass stopper was replaced with an addition funnel filled with 1,1,1,3,5,5,5-heptamethyl trisiloxane (27.50 g, 123.6 mmol). The 1,1,1,3,5,5,5-heptamethyl trisiloxane was added over a 28-minute period and then stirred and heated at 85° C. for 2.0 hours, and cooled to 65° C. The reaction mixture was then vacuum stripped at 50 torr from 65° C. to 90° C. for 0.25 hours, then at 90° C., 50 torr for 1.0 hour using a nitrogen sparge tube and a 90 degree inlet adapter attached to the vacuum line. After re-pressurization the flask, a 1.00 g sample was analyzed on a Mettler Toledo Moisture Analyzer (130° C., setting=3) and 99.70% solids were found. A yield of 121.9 g (93.8%) of an amber oil at 50° C. was obtained, which solidified into a gray wax at room temperature. The product was soluble in isopropanol and toluene, and at 50° C. it was a pourable liquid with 512 cP viscosity (measured with a Brookfield RV viscometer).

Preparation Example 8

Poly(co-ethyleneoxide-allyl glycidyl ether) with the average structure $HO(CH_2CH_2O)_{60.0}(CH2CH(CH_2OCH_2CH=CH_2)O)_{5.0}H$ (100.0 g, 157 mmol allyl), polymethylhydrogen siloxane $(CH_3)_3SiO[Si(CH_3)(H)O]_nSi(CH_3)_3$ (n is approximately 1.9) (7.19 g, 47.1 mmol), and toluene (32.0 g, 20.0 wt %) were charged into a 4-necked 250 mL round bottom flask, which was equipped with an overhead stirrer, thermocouple, Friedrich's condenser with nitrogen inlet, and a glass stopper. The mixture was heated to 85° C., then Karstedt's catalyst (diluted 1:9 in hexane, 8 ppm Pt) was added and the mixture was stirred for 1.2 hours. The reaction mixture was checked for hydrogen siloxanes by adding an aliquot to a fermentation tube filled with potassium hydroxide in ethanol. When no bubbles were detected it indicated that no hydrogen siloxanes were present.

Then further Karstedt's catalyst (diluted 1:9 in hexane, 8 ppm Pt) was added and the glass stopper was replaced with an addition funnel filled with 1,1,1,3,5,5,5-heptamethyl trisiloxane (20.5 g, 92.1 mmol). The 1,1,1,3,5,5,5-heptamethyl trisiloxane was added over a 16-minute period and then stirred and heated at 85° C. for 2.0 hours, and cooled to 50° C. The reaction mixture was then vacuum stripped at 50 torr from 50° C. to 90° C. for 1.0 hour, then at 90° C., 50 torr for 1.0 hour using a nitrogen sparge tube and a 90 degree inlet adapter attached to the vacuum line. After re-pressurization the flask, a 1.00 g sample was analyzed on a Mettler Toledo Moisture Analyzer (130° C., setting=3) and 99.60% solids were found. A yield of 119.2 g (93.4%) of an yellow oil at 50° C. was obtained, which solidified into a wax at room temperature. The product was soluble in isopropanol and toluene, and at 50° C. it was a pourable liquid with 1950 cP viscosity (measured with a Brookfield RV viscometer).

Preparation Example 9

Poly(co-ethyleneoxide-allyl glycidyl ether) with the average structure $HO(CH_2CH_2O)_{60.0}(CH2CH(CH_2OCH_2CH=CH_2)O)_{5.0}H$ (100.0 g, 157 mmol allyl), polymethylhydrogen siloxane $(CH_3)_3SiO[Si(CH_3)(H)O]_nSi(CH_3)_3$ (n is approximately 1.9) (6.00 g, 39.3 mmol), and toluene (32.0 g, 20.0 wt %) were charged into a 4-necked 250 mL round bottom flask, which was equipped with an overhead stirrer, thermocouple, Friedrich's condenser with nitrogen inlet, and a glass stopper. The mixture was heated to 85° C., then Karstedt's catalyst (diluted 1:9 in hexane, 8 ppm Pt) was added and the mixture was stirred for 1.2 hours. The reaction mixture was checked for hydrogen siloxanes by adding an aliquot to a fermentation tube filled with potassium hydroxide in ethanol. When no bubbles were detected it indicated that no hydrogen siloxanes were present.

Then further Karstedt's catalyst (diluted 1:9 in hexane, 8 ppm Pt) was added and the glass stopper was replaced with an addition funnel filled with 1,1,1,3,5,5,5-heptamethyl trisiloxane (22.2 g, 99.9 mmol). The 1,1,1,3,5,5,5-heptamethyl trisiloxane was added over a 30-minute period and then stirred and heated at 85° C. for 2.0 hours, and cooled to room temperature overnight. The reaction mixture was then vacuum stripped at 50 torr from 22° C. to 90° C. for 0.42 hours, then at 90° C., 50 torr for 1.0 hour using a nitrogen sparge tube and a 90 degree inlet adapter attached to the vacuum line. After re-pressurization the flask, a 1.00 g sample was analyzed on a Mettler Toledo Moisture Analyzer (130° C., setting=3) and 99.60% solids were found. A yield of 118 g (92%) of an yellow oil at 50° C. was obtained, which solidified into a wax at room temperature. The product was soluble in isopropanol and toluene, and at 50° C. it was a pourable liquid with 2175 cP viscosity (measured with a Brookfield RV viscometer).

TESTING EXAMPLES

The following testing examples illustrate the use of the cross-linked copolymer compositions in the present invention as demulsifying agents.
Testing Method
Crude oil demulsifiers were tested in the Middle East with fresh crude oil samples from three different oil fields. Field 1 produced medium heavy crude oil with about 25° API gravity, Field 2 produced a heavy crude oil with about 19° API and Field 3 produced medium heavy crude oil with about 28° API. The Following Test Method was used to Evaluate Demulsifiers:

The crude oil emulsions were tested near the wells, making sure that the samples were not older than 1-2 days. After homogenizing the sample by hand shaking, one hundred ml of crude oil emulsion was carefully poured into prescription glass bottles, which had marks at 10 mL intervals.

The various demulsifiers were added and the bottles were hand shaken 100 times and then the samples were kept in a water bath at the required temperature for a period of time characteristic of the separators at the field. The amount of the separated water was determined at regular intervals. At the end of the separation process the bottles were removed from the bath and the appearance of the separated crude oil, the separated water phase and crude oil/water interface, respectively, were observed. Then the amount of residual water and emulsion in the separated crude oil was determined, either in the "top cut" or in the "mixed cut". For the "top cut" a sample was taken from the top 80% of the separated crude oil phase and the residual water content was determined in two steps. First 50 parts (vol.) of crude oil sample was blended with 50 parts (vol.) of xylenes in a centrifuge tube (about 12.5 mL). Then this blend was vigorously shaken by hand and centrifuged for 5 min and the amount of separated water ("free water", W1) was recorded. Then two drops of a highly efficient demulsifier (knockout dropper) was added, followed by vigorous shaking and centrifuged again, to determine the total water (W2) content. The difference between the total and free water content is the unresolved emulsion (ΔW) and it characterized the efficiency of a demulsifier. The "mixed cut" was analyzed after the separation, by carefully siphoning out the separated water phase from the bottom of the bottles and then carefully homogenizing the sample by gentle hand-shaking. A sample from the homogenized crude was then analyzed by centrifugation as above. Prior to the bottle tests the free water and total water contents of the untreated crude oil were determined using the centrifugation methods above.

In the testing examples the preparation example copolymers were dissolved in various solvents.
Organic Demulsifiers:
Org 1, Org 2 and Org 3 were fully formulated organic demulsifier packages, which are developed for Field 1, Field 2 and Field 3 or typically used there.

Testing Example 1

Separation of Crude Oil Emulsion from Field 1

The original crude oil emulsion sample contained 2% free water and 24% total water. Table 1 shows the results at 60° C. using Org1 formulation with and without the silicone examples, respectively. The example copolymers were dosed separately, after dissolving them either in xylenes (XYL) or isopropanol (IPA). When the silicone was also added the organic demulsifier dose was halved.

TABLE 1

Bottle tests with crude oil emulsion from Field 1, at 60° C.

| # | Demulsifier | Actives Dose ppm | WATER DROP | | | | TOP CUT (80%) | | | | MIXED CUT | | | |
|---|---|---|---|---|---|---|---|---|---|---|---|---|---|---|
| | | | 30 min | 90 min | 1 h | 2 h | W1 | W2 | ΔW | Em. | W1 | W2 | ΔW | Em. |
| 1 | Org1 | 100 | 9 | 15 | 17 | 18 | 9.0 | 10 | 1.0 | 1 | 9 | 11 | 2 | tr |
| 2 | Org1 | 50 | 0 | 7 | 11 | 15 | 8.0 | 11 | 3.0 | 1 | 7 | 11 | 4 | 3 |
| 3 | Org1 + Ex. 1 (IPA) | 50 + 2.5 | tr | 13 | 16 | 20 | 8.0 | 9 | 1.0 | tr | 8 | 11 | 3 | 2 |
| 4 | Org1 + Ex. 1 (XYL) | 50 + 2.5 | 2 | 13 | 16 | 17 | 12.0 | 14 | 2.0 | 1 | 6 | 10 | 4 | 3 |
| 5 | Org1 + Ex. 1 (IPA) | 50 + 2.5 | 5 | 15 | 17 | 20 | 6.0 | 9.0 | 3.0 | 0.0 | 8.0 | 10.0 | 2 | 1.0 |
| 6 | Org1 + Ex. 1 (XYL) | 50 + 2.5 | 5 | 16 | 18 | 20 | 12.0 | 14.0 | 2.0 | 1.0 | 12.0 | 15.0 | 3 | 1.0 |
| 7 | Org1 + Ex. 2 (IPA) | 50 + 2.5 | 5 | 15 | 15 | 18 | 10.0 | 13.0 | 3.0 | 1.0 | | | | |
| 8 | Org1 + Ex. 2 (IXYL) | 50 + 2.5 | 9 | 16 | 19 | 20 | 6.0 | 10.0 | 4.0 | 4.0 | | | | |
| 9 | Org1 + Ex. 3 (IPA) | 50 + 2.5 | 3 | 12 | 15 | 19 | 8.0 | 10.0 | 2.0 | 0.0 | 5.6 | 10.0 | 4.4 | 4.4 |
| 10 | Org1 + Ex. 3 (IXYL) | 50 + 2.5 | 5 | 15 | 17 | 21 | 10.0 | 12.0 | 2.0 | 0.0 | 12.0 | 15.0 | 3 | 4.0 |
| 11 | Org1 + Ex. 1 (IPA) | 50 + 2.5 | 5 | 15 | 15 | 20 | 8.0 | 10.0 | 2.0 | 1.0 | | | | |
| 12 | Org1 + Ex. 1 (XYL) | 50 + 2.5 | 9 | 17 | 17 | 20 | 8.0 | 9.0 | 1.0 | tr | | | | |
| 13 | Blank | 0 | | | | tr | | | | | | | | | tr: trace

Testing Example 2

Separation of Crude Oil Emulsion from Field 1

The same crude oil emulsion was tested again as in Testing example 1 and Table 2 shows the results at 60° C.

TABLE 2

Bottle tests with crude oil emulsion from Field 1, at 60° C.

| # | Demulsifier | Actives Dose ppm | WATER DROP | | | | TOP CUT (80%) | | | | MIXED CUT | | | |
|---|---|---|---|---|---|---|---|---|---|---|---|---|---|---|
| | | | 10 min | 20 min | 40 min | 60 min | W1 | W2 | ΔW | Em. | W1 | W2 | ΔW | Em. |
| 1 | Org1 | 100 | 9 | 15 | 20 | 21 | 7.0 | 9 | 2.0 | 1 | 6 | 10 | 4 | 4 |
| 2 | Org1 | 50 | 3 | 12 | 15 | 15 | 5.6 | 10 | 4.4 | 2.4 | 7 | 12 | 5 | 3 |
| 3 | Org1 + Ex. 1 (XYL) | 50 + 2.5 | 5 | 15 | 18 | 17 | 11.0 | 14 | 3.0 | 1 | 7 | 13 | 6 | 5 |
| 4 | BLANK | 0 | 0 | 0 | 0 | tr | | | | | | | | |

Testing Example 3

Separation of Crude Oil Emulsion from Field 1

The original crude oil emulsion sample contained 8% free water and 18% total water. Table 3 shows the results at 40° C. using Org1 formulation with and without the silicone examples, respectively. Ex.2 preparation example was dissolved either in xylenes (XYL) or in dipropylene glycol monomethyl ether (DPM) obtained as Dowanol DPM from The Dow Chemical Company (Midland, Mich., USA) and then it was added either separately or after blending with Org1.

TABLE 3

Bottle tests with crude oil emulsion from Field 1, at 40° C.

| # | Demulsifier | Actives Dose ppm | WATER DROP 20 h | TOP CUT (80%) | | | | MIXED CUT | | | |
|---|---|---|---|---|---|---|---|---|---|---|---|
| | | | | W1 | W2 | ΔW | Em. | W1 | W2 | ΔW | Em. |
| 1 | Org1 | 50 | 9 | 9.0 | 13 | 4.0 | 3 | 8 | 10 | 2 | 2 |
| 2 | Org1 | 100 | 14 | 5.2 | 8 | 2.8 | tr | 6.5 | 9 | 2.5 | 1.5 |
| 3 | Org1 + Ex. 2 (XYL)* | 50 | 11 | 10.0 | 15 | 5.0 | nr | | | | |
| 4 | Org1 + Ex. 2 (DPM)* | 50 | 10 | 8.0 | 11 | 3.0 | 1 | | | | |
| 5 | Org1 + Ex. 2 (XYL) | 50 + 2.5 | 9 | 11.0 | 15 | 4.0 | nr | | | | |

TABLE 3-continued

| | | | WATER | | | | | | | | |
|---|---|---|---|---|---|---|---|---|---|---|---|
| | | Actives Dose | DROP | TOP CUT (80%) | | | | MIXED CUT | | | |
| # | Demulsifier | ppm | 20 h | W1 | W2 | ΔW | Em. | W1 | W2 | ΔW | Em. |
| 6 | Org1 + Ex. 2 (DPM) | 50 + 2.5 | 9 | 8.0 | 11 | 3.0 | 2 | | | | |
| 7 | BLANK | | 0 | | | | | | | | |

Bottle tests with crude oil emulsion from Field 1, at 40° C.

*Ex. 2 solution was blended with Org1 prior to dosing

Testing Example 4

Separation of Crude Oil Emulsion from Field 1

The original crude oil emulsion sample contained 6% free water and 27% total water. Table 4 shows the results at 40° C. using Org1 formulation with and without the preparation example Ex.2, respectively. Ex.2 was dosed separately, after dissolving it in various solvents: PG: propylene glycol; PM: propylene glycol monomethyl ether obtained as Dowanol PM from The Dow Chemical Company (Midland, Mich., USA); MeOH: methanol; ARO: aromatic solvent; BG: ethylene glycol butyl ether. When the silicone was also added the organic demulsifier dose was halved.

TABLE 4

Bottle tests with crude oil emulsion from Field 1, at 40° C.

| | | Actives Dose | WATER DROP | TOP CUT (80%) | | | | MIXED CUT | | | |
|---|---|---|---|---|---|---|---|---|---|---|---|
| # | Demulsifier | ppm | 20 h | W1 | W2 | ΔW | Em. | W1 | W2 | ΔW | Em. |
| 1 | Org1 | 100 | 12 | 9.0 | 19 | 10.0 | 15 | 8 | 20 | 12 | 16 |
| 2 | Org1 | 50 | 28 | 0.8 | 5.6 | 4.8 | 5.2 | 4 | 10 | 6 | 6 |
| 3 | Org1 + Ex. 2 (XYL) | 50 + 2.5 | 16 | 7.0 | 16 | 9.0 | 13 | | | | |
| 4 | Org1 + Ex. 2 (PM) | 50 + 2.5 | 14 | 8.0 | 16 | 8.0 | 12 | | | | |
| 5 | Org1 + Ex. 2 (DPM) | 50 + 2.5 | 12 | 10.0 | 16 | 6.0 | 10 | 10 | 19 | 9 | 14 |
| 6 | Org1 + Ex. 2 (IPA) | 50 + 2.5 | 13 | 9.0 | 18 | 9.0 | 15 | | | | |
| 7 | Org1 + Ex. 2 (MeOH) | 50 + 2.5 | 13 | 10.0 | 20 | 10.0 | 16 | | | | |
| 8 | Org1 + Ex. 2 (PG) | 50 + 2.5 | 16 | 10.0 | 26 | 6.0 | 18 | 7 | 17 | 10 | 13 |
| 9 | Org1 + Ex. 2 (ARO) | 50 + 2.5 | 14 | 10.0 | 19 | 9.0 | 10 | | | | |
| 10 | Org1 + Ex. 2 (BG) | 50 + 2.5 | 13 | 10.0 | 18 | 8.0 | 10 | | | | |

Testing Example 5

Separation of Crude Oil Emulsion from Field 1

The original crude oil emulsion sample contained 6% free water and 27% total water. Table 5 shows the results at 60° C. using Org1 formulation with and without the silicone examples, respectively. Ex.2 silicone was dosed separately, after dissolving it either in xylenes (XYL) or propylene glycol monomethyl ether (PM).

TABLE 5

Bottle tests with crude oil emulsion from Field 1, at 60° C.

| | | Actives Dose | WATER DROP | | | | TOP CUT (80%) | | | | MIXED CUT | | | |
|---|---|---|---|---|---|---|---|---|---|---|---|---|---|---|
| # | Demulsifier | ppm | 10 min | 20 min | 30 min | 60 min | W1 | W2 | ΔW | Em. | W1 | W2 | ΔW | Em. |
| 1 | Org1 | 100 | 19 | 22 | 22 | 22 | 9.0 | 11 | 2.0 | 0 | 9 | 11 | 2 | 0 |
| 2 | Org1 | 50 | 9 | 13 | 15 | 16 | 17.0 | 22 | 5.0 | 1 | 16 | 22 | 6 | tr |
| 3 | Org1 + Ex. 2 (XYL) | 50 + 2.5 | 12 | 18 | 17 | 18 | 12.0 | 14 | 2.0 | 1 | 12 | 15 | 3 | tr |
| 4 | Org1 + Ex. 2 (PM) | 50 + 2.5 | 10 | 16 | 18 | 19 | 11.0 | 13 | 2.0 | 1 | 10 | 13 | 3 | tr |
| 5 | BLANK | 0 | tr | tr | tr | tr | | | | | | | | |

Testing Example 6

Separation of Crude Oil Emulsion from Field 1

The original crude oil emulsion sample contained 6% free water and 27% total water. Table 6 shows the results at 40° C. using Org1 formulation with and without Ex.2, respectively. Ex.2 silicone was dosed separately, after dissolving it either in xylenes (XYL) or propylene glycol monomethyl ether (PM).

TABLE 6

Bottle tests with crude oil emulsion from Field 1, at 40° C.

| # | Demulsifier | Actives Dose ppm | WATER DROP 18 h | TOP CUT (80%) | | | | MIXED CUT | | | |
|---|---|---|---|---|---|---|---|---|---|---|---|
| | | | | W1 | W2 | ΔW | Em. | W1 | W2 | ΔW | Em. |
| 1 | Org1 | 100 | 25 | 5.0 | 7.5 | 1.5 | 0 | 4 | 8 | 4 | 0 |
| 2 | Org1 | 50 | 25 | 3.2 | 8 | 4.8 | 0 | 2.8 | 8 | 5.2 | 0 |
| 3 | Org1 + Ex. 2 (XYL) | 50 + 2.5 | 24 | 7.0 | 12 | 5.0 | 0 | 3.8 | 8 | 4.4 | 0 |
| 4 | Org1 + Ex. 2 (PM) | 50 + 2.5 | 25 | 4.8 | 9 | 4.2 | 0 | 4.4 | 8.5 | 4.1 | 0 |
| 5 | BLANK | 0 | tr | | | | | | | | |

Testing Example 7

Separation of Crude Oil Emulsion from Field 2

The original crude oil emulsion sample contained 13% free water and 24% total water. Table 7 shows the results at 60° C. using Org1 formulation with and without Ex.2, respectively. Ex.2 silicone was dosed separately, after dissolving it either in xylenes (XYL) or propylene glycol monomethyl ether (PM).

TABLE 7

Bottle tests with crude oil emulsion from Field 2, at 60° C.

| # | Demulsifier | Actives Dose ppm | WATER DROP | | | | TOP CUT (80%) | | | | MIXED CUT | | | |
|---|---|---|---|---|---|---|---|---|---|---|---|---|---|---|
| | | | 10 min | 20 min | 30 min | 60 min | W1 | W2 | ΔW | Em. | W1 | W2 | ΔW | Em. |
| 1 | Org1 | 100 | 1 | 5 | 12 | 19 | 5.2 | 5.4 | 0.2 | 0 | 5 | 5 | 0 | 0 |
| 2 | Org1 | 50 | 1 | 2 | 7 | 14 | 5.6 | 7 | 1.4 | tr | 7 | 10 | 3 | 0 |
| 3 | Org1 + Ex. 2 (XYL) | 50 + 2.5 | 1 | 2 | 10 | 16 | 6.0 | 6.5 | 0.5 | 0 | 5.6 | 7 | 1.4 | 0 |
| 4 | Org1 + Ex. 2 (PM) | 50 + 2.5 | 1 | 5 | 10 | 16 | 6.0 | 7 | 1.0 | 0 | 5.2 | 7 | 1.8 | 0 |
| 5 | BLANK | 0 | tr | tr | tr | tr | | | | | | | | |

Testing Example 8

Separation of Crude Oil Emulsion from Field 2

The original crude oil emulsion sample contained 9% free water and 17% total water. Table 8 shows the results at 60° C. using Org1 and Org 2 formulations with and without silicone examples, which were dosed separately, after dissolving them in xylenes (XYL).

TABLE 8

Bottle tests with crude oil emulsion from Field 2, at 60° C.

| # | Demulsifier | Actives Dose ppm | WATER DROP 2 h | TOP CUT (80%) W1 | W2 | ΔW | Em. | MIXED CUT W1 | W2 | ΔW | Em. |
|---|---|---|---|---|---|---|---|---|---|---|---|
| 1 | Org1 | 100 | 13 | 4.4 | 4.4 | 0.0 | 0 | 4 | 4 | 0 | 0 |
| 2 | Org1 | 50 | 5 | 4.0 | 6 | 2.0 | 0.4 | 7 | 10 | 3 | tr |
| 3 | Org1 + Ex. 2 (XYL) | 50 + 2.5 | 6 | 5.2 | 6 | 0.8 | 0 | 5.2 | 7 | 1.8 | 0 |
| 4 | Org1 + Ex. 3 (XYL) | 50 + 2.5 | 8 | 4.4 | 6 | 1.6 | 0 | | | | |
| 5 | Org2 | 100 | 20 | 1.6 | 3.6 | 2.0 | 1.8 | 4 | 4 | 0 | tr |
| 6 | Org2 | 50 | 10 | 2.0 | 6 | 4.0 | 2.4 | 6 | 8 | 2 | 1 |
| 7 | Org1 + Ex. 2 (XYL) | 50 + 2.5 | 8 | 4.4 | 7 | 2.6 | 0.8 | 7 | 9 | 2 | 0 |
| 8 | Org1 + Ex. 3 (XYL) | 50 + 2.5 | 9 | 2.8 | 7 | 4.2 | 2.4 | | | | |
| 9 | BLANK | 0 | 0 | | | | | | | | |

Testing Example 9

Separation of Crude Oil Emulsion from Field 3

The original crude oil emulsion sample contained 2.2% free water and 32% total water. Table 9 shows the results at 60° C. using Org3 formulation with and without silicone example Ex.2. Ex. 2 was dosed separately, after dissolving it in various solvents: DPM: dipropylene glycol monomethyl ether obtained as Dowanol PM from The Dow Chemical Company (Midland, Mich., USA); PM: propylene glycol; XYL: xylene; IPA: isopropanol.

TABLE 9

Bottle tests with crude oil emulsion from Field 3, at 60° C.

| # | Chemical | Actives Dose ppm | WATER DROP 10 min | 20 min | 30 min | 60 min | TOP CUT (80%) W1 | W2 | ΔW | BS | MIXED CUT W1 | W2 | ΔW | BS |
|---|---|---|---|---|---|---|---|---|---|---|---|---|---|---|
| 1 | Org3 | 50 | 2 | 8 | 11 | 13 | 18.0 | 22 | 4.0 | 3 | 14 | 19 | 5 | 5 |
| 2 | Org3 + Ex. 2 (DPM) | 50 + 2.5 | 8 | 11 | 13 | 16 | 19.0 | 22 | 3.0 | 0 | 18 | 20 | 2 | tr |
| 3 | Org3 + Ex. 2 (PM) | 50 + 2.5 | 5 | 10 | 11 | 16 | 18.0 | 20 | 2.0 | 1 | 15 | 17 | 2 | tr |
| 4 | Org3 + Ex. 2 (XYL) | 50 + 2.5 | 6 | 10 | 12 | 15 | 16.0 | 20 | 4.0 | 0 | 16 | 19 | 3 | 0 |
| 5 | Org3 + Ex. 2 (IPA) | 50 + 2.5 | 4 | 8 | 9 | 13 | 18.0 | 20 | 2.0 | 0 | 17 | 20 | 3 | tr |

It can be seen in the testing examples above that combining small amount of silicones (typically 5%) with any of the organic formulations improved the crude oil separation by reducing the amount of unresolved emulsion (ΔW).

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges there between. Such ranges may be viewed as a Markush group or groups consisting of differing pairwise numerical limitations which group or groups is or are fully defined by its lower and upper bounds, increasing in a regular fashion numerically from lower bounds to upper bounds. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents (and patent applications) referenced herein are herewith and hereby specifically incorporated by reference in their entirety as though set forth in full.

What is claimed is:

1. A soluble or dispersible copolymer composition, comprising the reaction products of (a) a copolymer having the formula

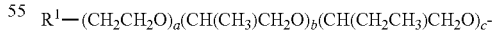

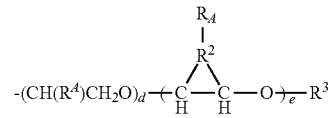

where $R^4$ is a monovalent group containing at least one terminal alkenyl group, such as an allyl (—$CH_2$—$CH$=$CH_2$), vinyl (—$CH$=$CH_2$) or methallyl (—$C(CH_3)$=$CH_2$) group, optionally containing heteroatoms and hydroxyl groups;

$R^1$ is selected from —OH, —OC(O)CH$_3$ or a monovalent hydrocarbon radical, optionally containing heteroatoms and hydroxyl groups, having from about 1 to about 40 carbon atoms;

$R^2$ is a trivalent hydrocarbon radical optionally containing heteroatoms and hydroxyl groups, having from about 3 to about 40 carbon atoms;

$R^3$ is selected from hydrogen, a —C(O)CH$_3$ group or a monovalent hydrocarbon radical optionally containing heteroatoms and hydroxyl groups, having from about 1 to about 40 carbon atoms;

and subscripts a, b, c, d and e are subject to the limitation 3<a+b+c+d+e<about 1000 and subscripts d+e≥2;

(b) a silicone hydride having the formula

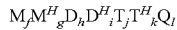

wherein
M=R$^4$R$^5$R$^6$SiO$_{1/2}$;
M$^H$=R$^7$R$^8$HSiO$_{1/2}$;
D=R$^9$R$^{10}$SiO$_{2/2}$;
D$^H$=R$^{11}$HSiO$_{2/2}$;
T=R$^{12}$SiO$_{3/2}$;
T$^H$=HSiO$_{3/2}$;
Q=SiO$_{4/2}$;
R$^4$, R$^5$, R$^6$, R$^7$, R$^8$, R$^9$, R$^{10}$, R$^{11}$ and R$^{12}$ are each independently selected from the groups of OR$^{13}$ or monovalent hydrocarbon radicals, optionally containing heteroatoms and hydroxyl groups, having from about 1 to about 20 carbon atoms;

R$^{13}$ is selected from the group of H or monovalent hydrocarbon radicals optionally containing heteroatoms and hydroxyl groups, having from about 1 to about 20 carbon atoms;

subscripts f, g, h, i, j, k and l are subject to the limitation 2<f+g+h+i+j+k+l<about 300, and g+i+k≥1;

and (c) a cross-linking agent.

2. The copolymer composition of claim 1 where $R^1$ is selected from —OH, —OC(O)CH$_3$ or a monovalent hydrocarbon radical, optionally containing heteroatoms and hydroxyl groups, having from about 1 to about 30 carbon atoms;

$R^2$ is a trivalent hydrocarbon radical optionally containing heteroatoms and hydroxyl groups, having from about 3 to about 30 carbon atoms;

$R^3$ is selected from hydrogen, a —C(O)CH$_3$ group or a monovalent hydrocarbon radical optionally containing heteroatoms and hydroxyl groups, having from about 1 to about 30 carbon atoms;

R$^4$, R$^5$, R$^6$, R$^7$, R$^8$, R$^9$, R$^{10}$, R$^{11}$ and R$^{12}$ are each independently selected from the group of OR$^{13}$ or monovalent hydrocarbon radicals, optionally containing heteroatoms and hydroxyl groups, having from about 1 to about 15 carbon atoms;

R$^{13}$ is selected from the group of H or monovalent hydrocarbon radicals optionally containing heteroatoms and hydroxyl groups, having from about 1 to about 15 carbon atoms.

3. A method for separating emulsions comprising
(i) combining a demulsifying composition comprising a blend of an emulsion and the copolymer composition of claim 2 to produce a blended composition;
(ii) allowing the blended composition to separate into at least two phases, and
(iii) separating said phases.

4. The copolymer composition of claim 1 where $R^1$ is selected from —OH, —OC(O)CH$_3$ or a monovalent hydrocarbon radical, optionally containing heteroatoms and hydroxyl groups, having from about 1 to about 20 carbon atoms;

$R^2$ is a trivalent hydrocarbon radical optionally containing heteroatoms and hydroxyl groups, having from about 3 to about 20 carbon atoms;

$R^3$ is selected from hydrogen, a —C(O)CH$_3$ group or a monovalent hydrocarbon radical optionally containing heteroatoms and hydroxyl groups, having from about 1 to about 20 carbon atoms;

R$^4$, R$^5$, R$^6$, R$^7$, R$^8$, R$^9$, R$^{10}$, R$^{11}$ and R$^{12}$ are each independently selected from the groups of OR$^{13}$ or monovalent hydrocarbon radicals, optionally containing heteroatoms and hydroxyl groups, having from about 1 to about 10 carbon atoms;

R$^{13}$ is selected from the group of H or monovalent hydrocarbon radicals optionally containing heteroatoms and hydroxyl groups, having from about 1 to about 10 carbon atoms.

5. A method for separating emulsions comprising
(i) combining a demulsifying composition comprising a blend of an emulsion and a copolymer composition of claim 4 to produce a blended composition;
(ii) allowing the blended composition to separate into at least two phases, and
(iii) separating said phases.

6. The copolymer composition of claim 1 where said cross-linking agent (c) is a silicone hydride, having the formula

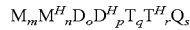

wherein
M=R$^{14}$R$^{15}$R$^{16}$SiO$_{1/2}$;
M$^H$=R$^{17}$R$^{18}$HSiO$_{1/2}$;
D=R$^{19}$R$^{20}$SiO$_{2/2}$;
D$^H$=R$^{21}$HSiO$_{2/2}$;
T=R$^{22}$SiO$_{3/2}$;
T$^H$=HSiO$_{3/2}$;
Q=SiO$_{4/2}$;
R$^{14}$, R$^{15}$, R$^{16}$, R$^{17}$, R$^{18}$, R$^{19}$, R$^{20}$, R$^{21}$ and R$^{22}$ are each independently selected from the groups of OR$^{23}$ or monovalent hydrocarbon radicals, optionally containing heteroatoms and hydroxyl groups, having from about 1 to about 20 carbon atoms;

R$^{23}$ is independently selected from the group of H or monovalent hydrocarbon radicals, optionally containing heteroatoms and hydroxyl groups, having from about 1 to about 20 carbon atoms;

subscripts m, n, o, p, q, r and s are subject to the limitation 1≤m+n+o+p+q+r+s<about 300.

7. A method for separating emulsions comprising
(i) combining a demulsifying composition comprising a blend of an emulsion and a copolymer composition of claim 6 to produce a blended composition;
(ii) allowing the blended composition to separate into at least two phases, and
(iii) separating said phases.

8. The copolymer composition of claim 1 where said cross-linking agent (c) is an organosilane, having the formula

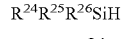

Wherein R$^{24}$, R$^{25}$ and R$^{26}$ each independently selected from the group of H or monovalent hydrocarbons having from about 1 to about 15 carbon atoms, preferably from about 1 to about 12 carbon atoms and more preferably from about 1 to about 10 carbon atoms, optionally containing nitrogen or oxygen or $OR^{27}$, subject to the limitation that the sum of the SiH and $OR^{27}$ groups in cross-linking agent (c) is more than one;

$R^{27}$ is independently selected from H or monovalent hydrocarbons having from about 1 to about 15 carbon atoms, preferably from about 1 to about 12 carbon atoms and more preferably from about 1 to about 10 carbon atoms, optionally containing nitrogen or oxygen.

9. A method for separating emulsions comprising:
(i) combining a demulsifying composition comprising a blend of an emulsion and a copolymer composition of claim 8 to produce a blended composition;
(ii) allowing the blended composition to separate into at least two phases, and
(iii) separating said phases.

10. The copolymer composition of claim 1 where said silicon hydride (b) has the formula $$MD_t D^H_u M$$

wherein
$M = R^{28} R^{29} R^{30} SiO_{1/2}$,
$D = R^{31} R^{32} SiO_{2/2}$,
$D^H = R^{33} HSiO_{2/2}$;
$R^{28}$, $R^{29}$, $R^{30}$, $R^{31}$, $R^{32}$ and $R^{33}$ are each independently selected from the group of $OR^{34}$ or monovalent hydrocarbon radicals, optionally containing heteroatoms and hydroxyl groups, having from about 1 to about 20 carbon atoms;
$R^{34}$ is independently selected from the group of H or monovalent hydrocarbon radicals, optionally containing heteroatoms and hydroxyl groups, having from about 1 to about 20 carbon atoms;
subscripts t and u are subject to the limitations $1 \leq t+u <$ about 300 and $1 \leq u$.

11. A method for separating emulsions comprising
(i) combining a demulsifying composition comprising a blend of an emulsion and a copolymer composition of claim 10 to produce a blended composition;
(ii) allowing the blended composition to separate into at least two phases, and
(iii) separating said phases.

12. The copolymer composition of claim 1 where said cross-linking agent (c) is a silicone hydride having the formula $$MD_v D^H_w M$$

wherein
$M = R^{35} R^{36} R^{37} SiO_{1/2}$;
$D = R^{38} R^{39} SiO_{2/2}$;
$D^H = R^{40} HSiO_{2/2}$;
$R^{35}$, $R^{36}$, $R^{37}$, $R^{38}$, $R^{39}$ and $R^{40}$ are each independently selected from the group of $OR^{41}$ or monovalent hydrocarbon radicals, optionally containing heteroatoms and hydroxyl groups, having from about 1 to about 20 carbon atoms, subject to the limitation that the sum of the SiH and $OR^{41}$ groups in cross-linking agent (c) is more than one;

$R^{41}$ is independently selected from the group of H or monovalent hydrocarbon radicals optionally containing heteroatoms and hydroxyl groups, having from about 1 to about 20 carbon atoms;
subscripts v and w are subject to the limitation $1 \leq v+w <$ about 300.

13. A method for separating emulsions comprising
(i) combining a demulsifying composition comprising a blend of an emulsion and a copolymer composition of claim 12 to produce a blended composition;
(ii) allowing the blended composition to separate into at least two phases, and
(iii) separating said phases.

14. The copolymer composition of claim 1 where said reaction products are further reacted with water.

15. A composition comprising a blend of
(i) an emulsion, and
(ii) a demulsifying-effective amount of said copolymer composition of claim 1.

16. The demulsifying composition in claim 15 where said emulsion is an emulsion comprising crude oil.

17. The demulsifying composition of claim 15 where said composition further comprises an additional demulsifier selected from the group consisting of organic or silicone demulsifiers or mixtures thereof wherein the weight ratio of the reaction products of claim 1 to the total amount of organic and silicone demulsifiers is in the range of about 100:1 to about 1:1000.

18. A method for separating emulsions comprising
(i) combining a demulsifying composition comprising a blend of an emulsion and a copolymer composition of claim 1 to produce a new composition;
(ii) allowing the new composition to separate into at least two phases, and
(iii) separating said phases.

19. The method for separating emulsions of claim 18 wherein blend further comprises an additional demulsifier selected from the group consisting of organic or silicone demulsifiers or mixtures thereof wherein the weight ratio of the reaction products of claim 1 to the total amount of organic and silicone demulsifiers is in the range of about 100:1 to about 1:1000.

20. The method for separating emulsions of claim 18 wherein the concentration of said demulsifying-effective amount of the reaction products is from about 0.1 ppm to about 10,000 ppm.

21. The reaction products of claim 1 wherein said composition further comprises an additional demulsifier selected from the group consisting of organic or silicone demulsifiers or mixtures thereof wherein the weight ratio of the reaction products of claim 1 to the total amount of organic and silicone demulsifiers is in the range of about 100:1 to about 1:1000.

22. The method of reacting copolymer (a) and cross-linking agent (c) in claim 1, followed by reaction with silicone hydride (b) in claim 1.

* * * * *